United States Patent [19]

Seite et al.

[11] Patent Number: 4,511,743

[45] Date of Patent: Apr. 16, 1985

[54] PROCESS FOR HOMOLOGATING ALCOHOLS THROUGH THE INTERMEDIATE PRODUCTION OF KETALS WITH COBALT CARBONYL COMPLEXES AS CATALYSTS

[75] Inventors: Claude Seite, Creteil; Dominique Commereuc, Meudon; Yves Chauvin, Le Pecq, all of France

[73] Assignee: Institut Francais du Petrole, Rueil-Malmaison, France

[21] Appl. No.: 548,737

[22] Filed: Nov. 4, 1983

[30] Foreign Application Priority Data

May 11, 1982 [FR] France ............... 82 18737

[51] Int. Cl.$^3$ .............................. C07C 27/20
[52] U.S. Cl. .................... 568/814; 568/715; 568/882; 568/883; 568/909
[58] Field of Search ............... 568/715, 814, 882, 883, 568/909

[56] References Cited

U.S. PATENT DOCUMENTS

| | | | |
|---|---|---|---|
| 4,133,966 | 1/1979 | Pretzer et al. | 568/883 |
| 4,190,729 | 2/1980 | Forster | 568/487 |
| 4,400,551 | 8/1983 | Keim et al. | 568/487 |
| 4,401,834 | 8/1983 | King | 568/881 |
| 4,424,383 | 1/1984 | Cornils et al. | 568/902 |
| 4,429,165 | 1/1984 | Wegman | 568/487 |

OTHER PUBLICATIONS

Wender et al., "Organic Synthecol via Metal Carbonyls", vol. 2, Wiley, 1977, pp. 26 to 32.

*Primary Examiner*—Werren B. Lone
*Attorney, Agent, or Firm*—Millen & White

[57] ABSTRACT

Process for the homologation of an alcohol wherein a ketal of the alcohol is reacted with hydrogen and carbon monoxide in the presence of a cobalt carbonyl complex and the resultant product is hydrolyzed to yield the aldehyde with one more carbon atom.

16 Claims, No Drawings

PROCESS FOR HOMOLOGATING ALCOHOLS THROUGH THE INTERMEDIATE PRODUCTION OF KETALS WITH COBALT CARBONYL COMPLEXES AS CATALYSTS

BACKGROUND OF THE INVENTION

The object of the present invention is a process for homologating alcohols through the intermediate production of ketals with cobalt carbonyl complexes as catalysts.

The alcohol homologation producing, by reaction with carbon monoxide and hydrogen, the alcohol and/or aldehyde with one additional carbon atom, can be written:

$$ROH + CO + 2H_2 \rightarrow R-CH_2OH + H_2O$$

and/or $$ROH + CO + H_2 \rightarrow R-CHO + H_2O$$

This reaction has long been known and is usually catalyzed by cobalt carbonyl complexes, such as, for example, dicobalt octacarbonyl. It is however necessary, for obtaining a reasonably fast conversion, to operate under severe temperature and pressure conditions, and by-products are formed in substantial amounts.

It has been proposed to add various promoters to the catalyst, in order to improve its activity. Among them, iodine and iodine compounds occupy a major place. There can be used an organic iodine compound, such as an alkyl iodide, or an inorganic iodine derivative, such as an alkali metal iodide. Recently the joint use of an organic iodide and an inorganic iodide has been claimed to improve the conversion of methanol to ethyl compounds, ethanol and/or acetaldehyde.

However the iodine derivatives have the disadvantage, in addition to their cost which makes their recycling necessary, to leave traces of iodine in the products which are thus polluted and even sometimes made unsuitable for certain purposes. This is, for example, the case of 2-phenyl ethanol, which could be prepared by homologation of benzyl alcohol but which must be made completely free of iodine for use in the perfume industry.

The homologation of acetals by carbonylation has also been described in the literature (I. Wender and P. Pino, Organic Syntheses via Metal Carbonyls, vol-2, J. Wiley, 1977, pages 26 to 32), but the reacting portion is the aldehyde portion of the acetal, in any case under very severe conditions, and not the alcohol portion.

The carbonylation of orthoesters (Wender and Pino, already mentioned) leads conversely, under mild conditions (100° C., 150 bars of $H_2 + CO$ synthesis gas) to the homologation of the alcohol portion of the molecule, which could thus contitute an alternative way to homologate an alcohol. Unhappily, the synthesis of orthoesters is difficult and requires costly and difficultly available reactants.

It has been found, and this constitutes the object of the invention, that the carbonylation of ketals results in the homologation of the alcohol portion of the ketal with high yields under mild conditions. The main product is the acetal of the homologous aldehyde in admixture with a low proportion of free homologous aldehyde. This acetal can be easily hydrolysed to aldehyde. The reaction is much faster than the homologation of the corresponding alcohol under the same conditions, and the selectivity to homologous products is higher.

DETAILED DISCUSSION

Contrarily to the orthoesters, the ketals can be synthesized easily by direct reaction of a ketone with an alcohol in acid medium.

The reaction scheme is the following:

$$2R_1R_2C=O + 4ROH \rightleftharpoons 2R_1R_2C(OR)_2 + 2H_2O \quad (1)$$

$$2R_1R_2C(OR)_2 + CO + H_2 \rightarrow \quad (2)$$
$$R-CH(OR)_2 + 2R_1R_2C=O + ROH$$

$$R-CH(OR)_2 + H_2O \rightleftharpoons R-CHO + 2ROH \quad (3)$$

---

$$ROH + CO + H_2 \rightarrow R-CHO + H_2O$$

This reaction is of general use and applies to varied ketals. The groups R, $R_1$ and $R_2$ of the equations (1) to (3) can be alkyl groups with 1 to 10 carbon atoms, or aralkyl or aryl groups with 6 to 15 carbon atoms, optionally carrying functional substituents which do not affect the reaction.

Non-limitative examples comprise, for example, the homologation of methanol to acetaldehyde through 2,2-dimethoxy propane (reaction with acetone), 2,2-dimethoxy butane (reaction with methylethylketone), 1,1-dimethoxy cyclohexane (reaction with cyclohexanone) or 2,2-dimethoxy-1,1,1,3,3,3-hexafluoro propane (reaction with hexafluoroacetone), the homologation of ethanol to propionaldehyde through 2,2-diethoxy propane, the homologation of benzyl alcohol to 2-phenyl ethanol through 2,2-dibenzoxy propane or 1,1-dibenzoxy cyclohexane.

In the process of the invention, the ketal can be carbonylated in batch in an autoclave, or in a continuous plant. The ketal can be prepared in a preliminary step distinct from the carbonylation by reacting the alcohol and the ketone under conditions described in the literature. It can also be generated in situ in the carbonylation reactor. It can also be prepared by exchange with the ketal of another less reactive alcohol, either in situ or prior to the reaction.

The aldehyde obtained by hydrolysis of the acetal, which is the main product of the carbonylation, is easily hydrogenated to the alcohol homologous to the starting alcohol.

The carbonylation may be performed with the pure ketal or the ketal dissolved in a solvent, such as a hydrocarbon, an ether or an alcohol less reactive than the alcohol to be homologated.

The carbonylation catalyst is a cobalt carbonyl complex which can be introduced into the reaction medium as dicobalt octacarbonyl, cobalt tetracarbonyl hydride, cobalt acetate or any cobalt compound generally used in the so-called "oxo" reactions. The cobalt concentration, expressed as the cobalt/ketal molar ratio, may be 0.1 to 0.0001 mole/mole, preferably 0.05 to 0.001 mole/mole. Cocatalysts can be used, specially those proposed in the past for the alcohol homologation reaction.

The synthesis gas used in the reaction has a hydrogen/carbon monoxide molar ratio of 0.5/1 to 3/1, preferably 1/1 to 2/1.

Although the pressure and temperature conditions depend on the ketal to be reacted, the pressure ranges from 10 to 25 MPa and the temperature from 70° to 220° C.

The following examples illustrate the invention, without limiting the scope thereof.

EXAMPLE 1

1.75 mmole of dicobalt octacarbonyl $Co_2(CO)_8$ and 0.39 mole of 1,1-dimethoxy cyclohexane are introduced, in the absence of air, into a stainless steel autoclave of 300 cc capacity equipped with a device regulating the temperature by electric heating and with a magnetic stirrer. The reactor is closed and scavenged three times with hydrogen under 1 MPa pressure. The pressure is raised to 12 MPa with synthesis gas having a molar $H_2/CO$ ratio of 1/1, and the temperature is raised to 120° C.

After a 2 hours reaction, the autoclave is cooled and its contents analysed by vapor phase chromatography. The conversion of 1,1-dimethoxy cyclohexane is 95%. The main product is 1,1-dimethoxy ethane, obtained with a yield of 25% (0.05 mole). Ethanol and acetaldehyde are present as traces. 1,1 dimethoxy ethane is hydrolysed to acetaldehyde which is then hydrogenated to ethanol with an overall yield of 90% for these two steps.

EXAMPLE 2

1.75 mmole of $Co_2(CO)_8$ and 0.49 mole of 2,2-dimethoxy propane are reacted in the same apparatus and under the same conditions as in example 1. The mixture is pressurized to 12 MPa with a synthesis gas whose ratio $H_2/CO$ is 1/1 by mole and the temperature is raised to 170° C. After a 1 hour reaction, 0.11 mole of 1,1-dimethoxy ethane is obtained with a yield of 45%.

EXAMPLE 3

This example is given for comparison. 50 cc of methanol and 1.75 mmole of $Co_2(CO)_8$ are reacted in the same apparatus and under the same operating conditions as in example 1. The pressure is raised to 12 MPa with a synthesis gas $H_2/CO=1/1$ by mole and the temperature to 120° C. After a 8 hours reaction, the conversion of methanol is only 4.1% (yields: 0.5% ethanol and 3.6% 1,1-dimethoxy ethane).

The comparison with example 1 shows the far higher reactivity of the methyl group when engaged as ketal.

EXAMPLE 4

0.1 mole of benzyl alcohol, 50 cc of 2,2-dimethoxy propane and 1.75 mmole of $Co_2(CO)_8$ are reacted in the same apparatus and under to the same operating conditions as in example 1.

The pressure is raised to 12 MPa with a synthesis gas having a $H_2/CO$ molar ratio of 1/1 and the temperature to 100° C. After a 4 hour reaction, the conversion of benzyl alcohol is 92.4%.

The products are the following:
Toluene: 26.4% b.w
Benzaldehyde: 9.7% b.w
2-Phenyl acetaldehyde: 3.3% b.w
2-Phenyl acetaldehyde dimethylacetal: 60.6% b.w Neither 2-phenyl ethanol nor products resulting from an homologation of 2,2-dimethoxy propane are detected.

2-phenyl acetaldehyde dimethylacetal is then hydrolysed and then hydrogenated to supply 2-phenyl ethanol.

EXAMPLE 5

0.1 mole of benzyl alcohol, 50 cc of 1,1-dimethoxy cyclohexane and 1.75 mmole of $Co_2(CO)_8$ are reacted in the same apparatus and according to the same procedure as in example 1. The pressure is raised to 12 MPa with a synthesis gas $H_2/CO=1/1$ by mole and the temperature to 120° C. After a 5 hours reaction, the conversion of benzyl alcohol is 70%. The products are the following:
Toluene: 24.3% b.w
2-phenyl ethanol: 1.7% b.w
2-phenyl acetaldehyde dimethylacetal: 74.0% b.w No traces of products resulting from an homologation of 1,1-dimethoxy cyclohexane are detected.

EXAMPLE 6

This example is given by way of comparison. 0.4 mole of benzyl alcohol and 5 mmole of $Co_2(CO)_8$ are reacted in the same apparatus and under the same conditions as in example 1. The pressure is raised to 12 MPa with a synthesis gas having a $H_2/CO$ molar ratio of 1/1 and the temperature to 120° C. After a 8 hour reaction, the conversion of benzyl alcohol is 57%. The products are the following:
Toluene: 55.9% b.w
Benzaldehyde: 2.5% b.w
2-phenyl acetaldehyde: 4.3% b.w
2-phenyl ethanol: 37.3% b.w The comparison with example 5 shows that, in the absence of a precursor of benzyl ketal, the reaction is much slower and the selectivity to homologous products smaller, although the proportion of catalyst was greater.

What is claimed is:

1. A process for converting an alcohol to the acetal of its next higher homolog aldehyde, comprising the steps of reacting the alcohol with a ketone, or a ketal thereof with a less reactive alcohol, under conditions wherein the alcohol is converted to its corresponding ketal; contacting the resultant ketal with synthesis gas comprising carbon monoxide and hydrogen, in the presence of an effective catalytic amount of a cobalt carbonyl complex; and recovering resultant acetal of the next higher homolog aldehyde of said alcohol.

2. A process according to claim 1, wherein the ketal is prepared in a separate step, prior to the homologation step, by reacting the alcohol with a ketone and recovering the resultant ketal.

3. A process according to claim 1, wherein the ketal is prepared in situ, during the course of the homologation reaction, by reacting the alcohol with a ketone or by exchange with the ketal of an alcohol of lower reactivity under the homologation conditions.

4. A process according to claim 1, wherein the alcohol is methanol.

5. A process according to claim 1, wherein the alcohol is benzyl alcohol.

6. A process according to claim 1, wherein the ketal is the product of reaction of the alcohol with acetone, cyclohexanone, methyl ethyl ketone or hexafluoroacetone.

7. A process according to claim 1, wherein the ketal of the alcohol subjected to homologation is prepared by exchange with 2,2-dimethoxy propane or 1,1-dimethoxy cyclohexane.

8. A process according to claim 1, wherein the catalyst is dicobalt octacarbonyl.

9. A process according to claim 1, wherein said contacting is effected at a temperature of 70°–220° C., and a pressure of 10–25 MPa; and wherein the synthesis gas has a molar ratio $H_2/CO$ of 0.5/1–3/1.

10. A process according to claim 1, which further comprises hydrolyzing the resultant acetal of the next higher homolog aldehyde of said alcohol, and recovering resultant next higher homolog aldehyde of said alcohol.

11. A process according to claim 10, which further comprises hydrogenating the resultant next higher homolog aldehyde, and recovering resultant next higher homolog of said alcohol.

12. A process according to claim 1, wherein said alcohol has the formula ROH, wherein R is a substituted or unsubstituted alkyl group having 1–10 carbon atoms or a substituted or unsubstituted aralkyl or aryl group having 6–15 carbon atoms.

13. A process according to claim 1, wherein the molar ratio cobalt/ketal is 0.1–0.0001.

14. A process according to claim 13, wherein said molar ratio is 0.05–0.001.

15. A process according to claim 9, wherein the synthesis gas has a molar ratio $H_2/CO$ of 1/1–2/1.

16. A process for carbonylating a ketal, comprising the step of contacting the ketal with synthesis gas comprising carbon monoxide and hydrogen, in the presence of an effective catalytic amount of cobalt carbonyl complex, and recovering resultant acetal of the next higher homolog aldehyde of the alcohol component of said ketal.

* * * * *